United States Patent
Buvid et al.

(10) Patent No.: US 10,274,440 B2
(45) Date of Patent: Apr. 30, 2019

(54) METHOD TO FACILITATE INVESTIGATION OF CHEMICAL CONSTITUENTS IN CHEMICAL ANALYSIS DATA

(71) Applicant: International Business Machines Corporation, Armonk, NY (US)

(72) Inventors: Daniel J. Buvid, Rochester, MN (US); Eric J. Campbell, Rochester, MN (US); Tyler Jandt, Rochester, MN (US); Joseph Kuczynski, North Port, FL (US)

(73) Assignee: International Business Machines Corporation, Armonk, NY (US)

( * ) Notice: Subject to any disclaimer, the term of this patent is extended or adjusted under 35 U.S.C. 154(b) by 366 days.

(21) Appl. No.: 15/189,843

(22) Filed: Jun. 22, 2016

(65) Prior Publication Data

US 2017/0371497 A1 Dec. 28, 2017

(51) Int. Cl.
G06F 19/00 (2018.01)
G01N 23/20091 (2018.01)
G06T 11/20 (2006.01)

(52) U.S. Cl.
CPC ...... G01N 23/20091 (2013.01); G06T 11/206 (2013.01); G06T 2200/24 (2013.01)

(58) Field of Classification Search
CPC . G01J 3/28; G01J 2003/2833; G01N 30/8675
See application file for complete search history.

(56) References Cited

U.S. PATENT DOCUMENTS

| | | | |
|---|---|---|---|
| 5,710,713 A * | 1/1998 | Wright | G01N 21/274 250/282 |
| 6,289,287 B1 | 9/2001 | Meng et al. | |
| 6,480,755 B1 * | 11/2002 | Ootani | G05B 19/41865 700/105 |
| 6,581,013 B1 | 6/2003 | Annis et al. | |
| 6,625,546 B2 | 9/2003 | Sepetov et al. | |
| 6,703,228 B1 * | 3/2004 | Landers | C12Q 1/6827 435/6.11 |
| 7,820,378 B2 | 10/2010 | Van Den Boom et al. | |

(Continued)

OTHER PUBLICATIONS

EDAX-Smart Insight—"Spectrum Library Matching in TEAM Analysis", viewed Feb. 22, 2016, http://www.edax.com/products/eds/team/spectrum-library-matching.aspx.

(Continued)

*Primary Examiner* — Justin S Lee
(74) *Attorney, Agent, or Firm* — Patterson + Sheridan, LLP

(57) ABSTRACT

A method includes generating a graphical display based on chemical analysis data. The method also includes receiving input selecting a graphical component of the graphical display. The graphical component corresponds to a chemical or elemental constituent represented in the chemical analysis data. The method also includes receiving a specimen identifier indicating a specimen that was analyzed to generate the chemical analysis data. The method further includes generating a search query based on the specimen identifier and based on a constituent identifier of the chemical or elemental constituent and performing a search based on the search query to identify potential sources of the chemical or elemental constituent.

20 Claims, 6 Drawing Sheets

(56) References Cited

U.S. PATENT DOCUMENTS

| | | | |
|---|---|---|---|
| 8,526,723 B2 | 9/2013 | Prasad et al. | |
| 8,645,082 B2 | 2/2014 | Tan et al. | |
| 8,916,818 B2* | 12/2014 | Sekiya | G01N 30/8651 |
| | | | 250/281 |
| 9,797,866 B2* | 10/2017 | Carver | H01J 49/0031 |
| 2003/0233163 A1* | 12/2003 | Dorsch | G05B 19/41865 |
| | | | 700/117 |
| 2004/0003000 A1* | 1/2004 | Smith | G06F 19/702 |
| 2004/0199891 A1* | 10/2004 | Bentley | G06F 17/50 |
| | | | 716/102 |
| 2004/0265909 A1 | 12/2004 | Blaney et al. | |
| 2006/0186234 A1* | 8/2006 | Kerns | C10L 5/00 |
| | | | 241/16 |
| 2007/0016612 A1* | 1/2007 | James | G06F 19/705 |
| 2007/0233401 A1* | 10/2007 | Workman | G01J 3/02 |
| | | | 702/28 |
| 2008/0234948 A1* | 9/2008 | Walk | G01N 30/8675 |
| | | | 702/23 |
| 2009/0105983 A1* | 4/2009 | Variyam | G01R 31/319 |
| | | | 702/124 |
| 2009/0179147 A1* | 7/2009 | Milgram | G01N 30/8651 |
| | | | 250/282 |
| 2011/0064191 A1* | 3/2011 | Toth | G01N 23/20033 |
| | | | 378/53 |
| 2011/0066632 A1* | 3/2011 | Robson | G06F 19/705 |
| | | | 707/769 |
| 2011/0125477 A1* | 5/2011 | Lightner | G05B 13/048 |
| | | | 703/11 |
| 2012/0160999 A1* | 6/2012 | Zaluzec | H01J 37/244 |
| | | | 250/307 |
| 2013/0297254 A1* | 11/2013 | Vignesh | G01N 21/65 |
| | | | 702/179 |
| 2014/0324825 A1* | 10/2014 | Gopinath | G06F 17/30705 |
| | | | 707/722 |
| 2015/0286239 A1* | 10/2015 | Regier | G05F 3/16 |
| | | | 324/76.11 |
| 2015/0300944 A1* | 10/2015 | Pelletier | G01J 3/10 |
| | | | 356/436 |
| 2016/0025569 A1* | 1/2016 | Hargreaves | G01J 3/0291 |
| | | | 356/301 |
| 2016/0070807 A1* | 3/2016 | Epstein | G06F 17/30867 |
| | | | 707/706 |
| 2016/0267220 A1* | 9/2016 | Becker | G06F 19/24 |

OTHER PUBLICATIONS

Kusne, et al., "Machine Learning for High Throughput Materials Discovery and Optimization Applications", The National Institute of Standards and Technology (NIST), Material Measurement Laboratory, Jul. 9, 2013.

* cited by examiner

METHOD TO FACILITATE INVESTIGATION OF CHEMICAL CONSTITUENTS IN CHEMICAL ANALYSIS DATA

I. FIELD OF THE DISCLOSURE

The present disclosure relates generally to investigation of chemical constituents in chemical analysis data.

II. BACKGROUND

Spectroscopy began as the study of the absorption and emission of light or other electromagnetic radiation by matter. It later evolved to include the study of how samples of matter interact with other particles such as electrons, protons, and ions. Various types of spectrographic methods are used to study the interaction of a sample with radiation or particles. When trying to analyze spectra, it can be difficult to properly identify and distinguish low intensity spectral lines from background noise. This problem becomes even more difficult if the low intensity lines are associated with an element that would not typically be present in a given sample.

III. SUMMARY OF THE DISCLOSURE

This disclosure describes a computing device and process to facilitate investigation of elements and compounds present in a given sample.

According to an embodiment, a computing device includes a sensor interface to receive chemical analysis data, a processor coupled to the sensor interface, and a memory storing instructions executable by the processor. The processor generates a graphical display based on the chemical analysis data and receives input to select a graphical component of the graphical display. The graphical component corresponds to a chemical or elemental constituent represented in the chemical analysis data. The processor receives a specimen identifier that indicates a specimen that was analyzed to generate the chemical analysis data. The processor generates a search query based on the specimen identifier and based on a constituent identifier of the chemical or elemental constituent. The processor performs a search based on the search query to identify potential sources of the chemical or elemental constituent.

According to another embodiment, a method includes generating a graphical display based on chemical analysis data and receiving input that selects a graphical component of the graphical display. The graphical component corresponds to a chemical or elemental constituent represented in the chemical analysis data. The method also includes receiving a specimen identifier that indicates a specimen that was analyzed to generate the chemical analysis data. The method includes generating a search query based on the specimen identifier and based on a constituent identifier of the chemical or elemental constituent and performing a search based on the search query to identify potential sources of the chemical or elemental constituent.

According to another embodiment, a computer-readable storage device stores instructions executable by a processor. The instructions cause the processor to generate a graphical display based on chemical analysis data. The instructions also cause the processor to generate a search query based on a specimen identifier and based on a constituent identifier. The specimen identifier indicates a specimen that was analyzed to generate the chemical analysis data, and the constituent identifier corresponds to a chemical or elemental constituent represented in the chemical analysis data. The instructions also cause the processor to perform a search based on the search query to identify potential sources of the chemical or elemental constituent and to generate a search results display that includes a plurality of search results identified by the search.

Features and other benefits that characterize embodiments are set forth in the claims annexed hereto and forming a further part hereof. However, for a better understanding of the embodiments, and of the advantages and objectives attained through their use, reference may be made to the Drawings and to the accompanying descriptive matter.

IV. BRIEF DESCRIPTION OF THE DRAWINGS

V. DETAILED DESCRIPTION

Figure 1:
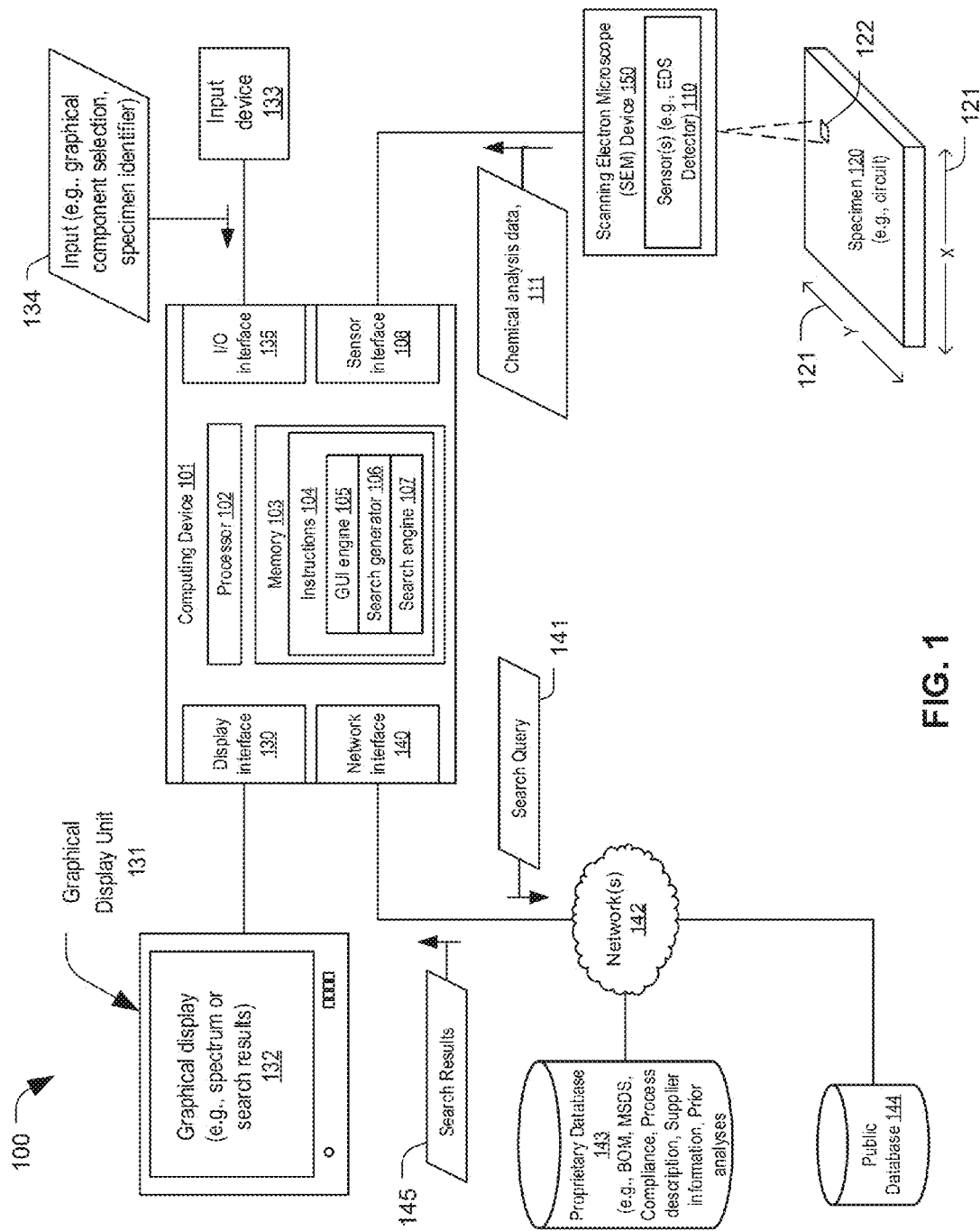
FIG. 1 is a diagram depicting an embodiment of a system to facilitate investigation of chemical constituents in chemical analysis data.

The present disclosure describes a computing device that is configured to perform a search based on specimen identifiers and constituent identifiers. The search facilitates identification of potential sources of chemical or elemental constituents of chemical analysis data. The present disclosure also describes processes for performing a search based on specimen identifiers and constituent identifiers to identify potential sources of chemical or elemental constituents of chemical analysis data.

According to an embodiment, a computing device includes a sensor interface to receive chemical analysis data, a processor coupled to the sensor interface, and a memory storing instructions executable by the processor. The computing device may be coupled to one or more sensors via the sensor interface. For example, the one or more sensors may include an electron microscope, an energy dispersive spectroscopy sensor, another spectroscopy device, or a combination thereof. The processor, executing instructions stored in the memory, is configured to generate a graphical display based on the chemical analysis data received via the sensor interface. The chemical analysis data may include, be included within, or correspond to an elemental analysis spectrum. A peak of the elemental analysis spectrum may be represented as a graphical component in the graphical display. The peak may represent a chemical or elemental constituent in the specimen analyzed by the one or more sensors.

As a particular example, the one or more sensors may include an Energy-dispersive X-ray spectroscopy (EDS) sensor. An EDS sensor may use a beam of charged particles focused into a sample of matter. The particles excite electrons of inner electron orbitals (e.g., an inner shell) of atoms in the sample. Occasionally, an electron is ejected from the inner shell of an atom creating an electron hole in the shell.

The electron hole may be filled by an electron from a higher energy orbital (e.g., an outer shell) dropping down to fill the electron hole. To fill the electron hole, the electron from the outer shell undergoes a reduction in energy by emitting energy as an X-ray (e.g., a photon in an X-ray wavelength). A detector detects photons emitted from the sample. The detector may count a number of photons detected in each of a set of energy levels. For example, each energy level may correspond to a range of kiloelectronvolt (keV) values. Each element emits photons at one or more characteristic energy levels. The number of photons detected in a particular energy level corresponds to an amplitude of a detection peak at the particular energy level. An analyzer plots the detected amplitudes at the various energy level as a plot of spectral lines. As each element has a unique set of spectral lines, analysis of the spectral lines indicates the composition of the sample.

The computing device may generate a graphical display of the set of spectral lines based on the chemical analysis data. A user of the computing device may use an input device (e.g., a pointing device, touch screen, a keyboard, etc.) to select a graphical component (e.g., a peak or spectral line) of the graphical display. The computing device may determine a constituent identifier that corresponds to the selected graphical component. For example, the graphical component may include a spectral line associated with (or indicative of) a particular element or a particular chemical (i.e., a chemical or elemental constituent of the specimen). In this example, the constituent identifier may include an identifier (e.g., a name, an atomic number, etc.) of the particular element or the particular chemical.

The computing device may also receive (or have access to) a specimen identifier that identifies the specimen that was analyzed to generate the chemical analysis data. For example, if the specimen includes a component of a circuit, the specimen identifier may include an identifier of the circuit, an identifier of the component, a location of the component, or a combination thereof. In other examples, the specimen identifier may include a part number, an assembly name, etc.

The computing device may generate a search query based on the specimen identifier and the constituent identifier. The computing device may perform a search based on the search query to identify potential sources of the chemical or elemental constituent. The search query may be used to query one or more proprietary databases, one or more publicly-available databases, or a combination thereof. Results of the search query may be compared to the chemical analysis data in order to prioritize the results for display. For example, if a first search result identifies a first chemical used to manufacture the specimen as a potential source of a first element detected in the chemical analysis data, and a second search result identifies a second chemical used to manufacture the specimen as a potential source of the first element, the computing device may determine whether a second element detected in the chemical analysis data is present in the first chemical or the second chemical. If the second element is present in the first chemical and is not present in the second chemical, the first chemical may be given a higher priority or more prominent position in a display of the search results. In other examples, other criteria may be used to sort the search results, such as when (in a manufacturing process) the specimen would have been exposed to particular chemicals, etc.

FIG. 1 is a diagram depicting an embodiment of a system to facilitate investigation of chemical constituents in chemical analysis data. The system 100 includes a computing device 101 and one or more sensors 110. The computing device 101 includes or is coupled to an input device 133 and a graphical display unit 131. The computing device 101 may also be connected (e.g., via a wired or wireless connection) to one or more networks 142. The computing device 101 includes a processor 102, a memory 103, a sensor interface 108, an input/output interface 135, a display interface 130, and a network interface 140. The memory 103 includes instructions 104 that are executable by the processor 102. For example, the instructions 104 may include a graphic user interface (GUI) engine 105, a search generator 106, and a search engine 107.

In the embodiment illustrated in FIG. 1, the sensors 110 are configured to generate chemical analysis data 111 by analyzing a specimen 120 or a portion of the specimen 120, such as a component at a location 122 on the specimen 120. The sensors 110 may include, be included within, or correspond to an electron microscope or an energy dispersive spectroscopy sensor, such as a scanning electron microscope (SEM) device 150. In other examples, the sensors 110 include or correspond to other types of sensors, such as mass spectrometers, optical spectrometers, and magnetic spectrometers.

The sensors 110, another component of the SEM device 150, or the computing device 101 may generate information indicating the location 122 on the specimen 120 scanned to generate particular data, such as chemical analysis data 111, a SEM image, or both. For example, the location 122 may be identified as positions along axes 121 of the specimen 120 or of a test platform. The sensor 110 may transmit the data, e.g., the chemical analysis data 111, to the sensor interface 108 of the computing device 101.

In the embodiment illustrated in FIG. 1, the processor 102 may execute the GUI engine 105 to generate a graphical display 132 (e.g., at the graphical display unit 131) based on data received from the sensors 110. For example, the graphical display 132 may represent spectral lines related to the chemical analysis data 111 obtained from the specimen 120.

The processor 102 may also execute the search generator (or another application or component of an operating system) to receive user input 134 from an input device 133. The input device 133 may include, be included within, or correspond to a mouse, a touch-sensitive computer screen, a keyboard, etc. When the graphical display 132 representing the chemical analysis data 111 is displayed, the user input 134 may select a graphical component of the graphical display 132. The graphical component may include a peak or spectral line associated with a chemical or elemental constituent represented in the chemical analysis data. Based on the user input 134, the computing device 101 may determine a constituent identifier that identifies the chemical or elemental constituent. For example, the peak or spectral line may be associated with a chemical or elemental constituent that is not expected to be present in the specimen. In this example, the user may select the peak or spectral line to determine an identification of the chemical or elemental constituent (e.g., an atomic number of an elemental constituent, or a name, molecular weight, or other identifier of a chemical constituent). As described further below, the computing device 101 may use the constituent identifier to perform a search to facilitate identification of a source of the chemical or elemental constituent.

In the embodiment illustrated in FIG. 1, the computing device 101 may receive a specimen identifier associated with the specimen 120. For example, the specimen identifier may be received from the SEM device 150, from the sensors 110, or from the memory 103, via user input 134, from another device, or a combination thereof. To illustrate, when a user sets up the SEM device 150, the user may provide information identifying the specimen 120 (e.g., a serial number of a device corresponding to the specimen 120). In this illustrative example, the SEM device 150 may provide the information identifying the specimen 120 with the chemical analysis data 111 or in addition to the chemical analysis data 111. The information identifying the specimen 120 may correspond to the specimen identifier or may be used by the computing device 101 to look up the specimen identifier (e.g., from the proprietary database 143). As another illustrative example, the sensors 110 may include an optical sensor, a radiofrequency identification (RFID) sensor, or another sensor that is able to read information identifying the specimen 120 from the specimen 120.

As a specific example, the specimen 120 may include a component of a circuit. In this example, the specimen identifier may include an identifier of the circuit and an identifier of a component of the circuit. To illustrate, the identifier of the component may identify the location 122 (e.g., a coordinate position) of the component on the specimen 120. Alternatively, or in addition, the identifier of the component may include a name, number, or other identifier denoting a discrete component (e.g., a resistor, a capacitor, an inductor, a switch, a transistor, etc.), a name, number, or identifier denoting a set of circuit elements (such as a block of logic, a memory cell, a set of memory cells, etc.), a name, number, or other identifier of a conductive trace or connector (e.g., a wire, a pad, a pin, etc.).

The processor 102 may execute instructions of the search generator 106 to a search query 141 based on the specimen identifier and the constituent identifier. For example, the search query 141 may identify the location 122 of the specimen 120 that was targeted to generate the chemical analysis data 111 and may include a name, number, or other identifier of a particular element or chemical represented in the chemical analysis data 111. The search query 141 or a portion thereof may be displayed in the graphical display 132 to enable the user to edit the search query 141 or to initiate a search based on the search query 141.

In the embodiment illustrated in FIG. 1, the processor 102 may execute instructions of the search engine 107 to perform a search based on the search query 141. For example, the computing device 101 may send the search query 141 to one or more databases via the one or more networks 142. The specific database(s) searched may be selected automatically by the search engine 107 (e.g., based on user specific settings or other configuration data stored in the memory 103), or the user may designate (via the input 134) the databases when the search query 141 is displayed. The databases may include proprietary databases 143, public databases 144, or both. Examples of proprietary databases 143 include supplier informational databases; databases that include results of prior analyses by the user or other users, results of prior analyses using the sensors 110, results of prior analyses using the SEM device 150, or a combinations thereof; process descriptions; compliance or regulatory databases; databases of material data safety sheets (MSDS); or bills of materials (BOM). The databases 143,144 return search results 145 to the computing device 101. The search results 145 may identify one or more potential sources of the chemical or elemental constituent associated with the constituent identifier.

In a particular embodiment, the graphical display 132 may be updated based on the search results 145. For example, the search results (or a portion thereof) may be displayed as an ordered list. In this example, the list may be ordered based on user configurable settings (e.g., a setting indicating a preference for a particular database). Alternatively or in addition, the list may be ordered based on relevance of particular search results. The relevance of the search results may be determined based on how closely each search result matches the chemical analysis data as a whole. To illustrate, a first search result may be associated with a first chemical, and a second search result may be associated with a second chemical. Both the first chemical and the second chemical may include an element identified by the constituent identifier in the search query 141. Accordingly, the first chemical and the second chemical may be compared to the chemical analysis data 111. If the first chemical includes at least one additional element that is identified in the chemical analysis data 111 and the second chemical does not include an additional element that is identified in the chemical analysis data 111, then the first search result (corresponding to the first chemical) may be assigned a higher priority in the order list of search results. Alternatively, in this example, if the first chemical includes two additional elements that are identified in the chemical analysis data 111 and the second chemical includes only one additional element that is identified in the chemical analysis data 111, then the first search result (corresponding to the first chemical) may be assigned a higher priority in the order list of search results.

Thus, the system 100 may facilitate identifying a source of the chemical or element constituent identified in the chemical analysis data 111. For example, if the chemical analysis data 111 indicates the presence of an element that is not expected to be present, the user can use the system 100 to implement a search for a source of the unexpected element. To illustrate, the search query 141 can be used to search the proprietary databases, which may include information descriptive of processes used to form the specimen 120 (e.g., process steps, process chemistry, etc.), a bill of materials associated with the specimen, MSDSs associated with a manufacturing area associated with the specimen 120, etc. Additionally, or in the alternative, the search query 141 can be used to search the public databases 144 based on an identifier of the element (e.g., the constituent identifier) and an identifier of the specimen (e.g., the specimen identifier). Accordingly, in this example, the system 100 may facilitate identifying a source of a contamination that resulted in the presence of the unexpected element. Of course, in other embodiments, the system 100 may be used to analyze other types of specimens and to generate search queries.

Figure 2:
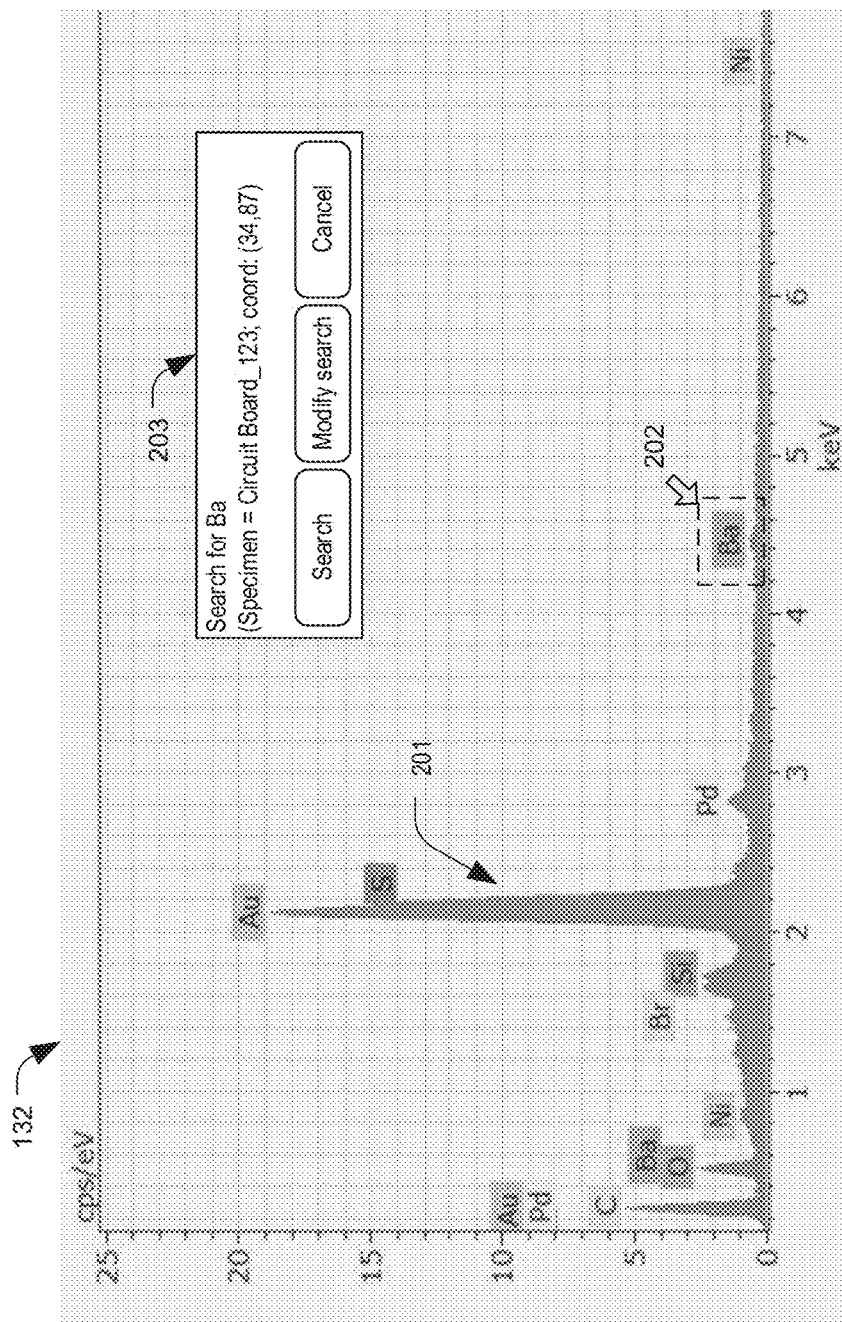
FIG. 2 is a graphical display of chemical analysis data and a search query generated by the system of FIG. 1, according to one embodiment.

FIG. 2 is a diagram depicting a graphical display 132 of the chemical analysis data 111, as generated by the system of FIG. 1. In FIG. 2, the graphical display 132 includes a search query command interface 203, according to a particular embodiment. The graphical display 132 may also depict a set of spectral lines or peaks 201 that correspond to the chemical or elemental constituents of the specimen 120.

In FIG. 2, a target peak 202 has been selected by a user (as indicated by a dashed box). For example, the target peak 202 may correspond to a chemical or elemental constituent of the chemical analysis data 111 that was not expected to be present in the specimen 120. Alternatively, the target peak 202 may be selected for another reason. In some implementations, the target peak 202 may be automatically selected by the computing device 101 of FIG. 1 in response to a determination that the target peak 202 corresponds to a chemical or elemental constituent of the chemical analysis data 111 that was not expected to be present in the specimen (e.g., based on expected chemical characteristics of the specimen stored in the memory 103 or in one of the databases 143, 144).

In a particular embodiment, the computing device 101 automatically displays the search query command interface 203 based on the targeted peak 202 being selected in the graphical display 132. The search query command interface 203 may include selectable options to initiate or configure a search. For example, the selectable options may include a search option that is selectable to send the search query 141 to the proprietary databases 143, to the public databases 144, or to both. As another example, the selectable options may include a modifiable search option that is selectable to enable the user to modify the search query 141. To illustrate, the user may designate particular databases to be searched, modify the specimen identifier, modify the constituent identifier, etc. As another example, the selectable options may include a cancel option to cancel the search, to close the search query command interface 203, or to allow the user to select a different target peak.

In the example illustrated in FIG. 2, the search query command interface 203 includes information identifying the target peak 202 (e.g., Ba for Barium). The search query command interface 203 may also include the specimen identifier or other information related to the specimen. To illustrate, in FIG. 2, the search query command interface 203 indicates that the chemical analysis data 111 represented in the graphical display 132 was determined based on analysis of a particular coordinate location ("coord: (34, 87)") of a particular circuit ("Circuit Board_123").

Figure 3:
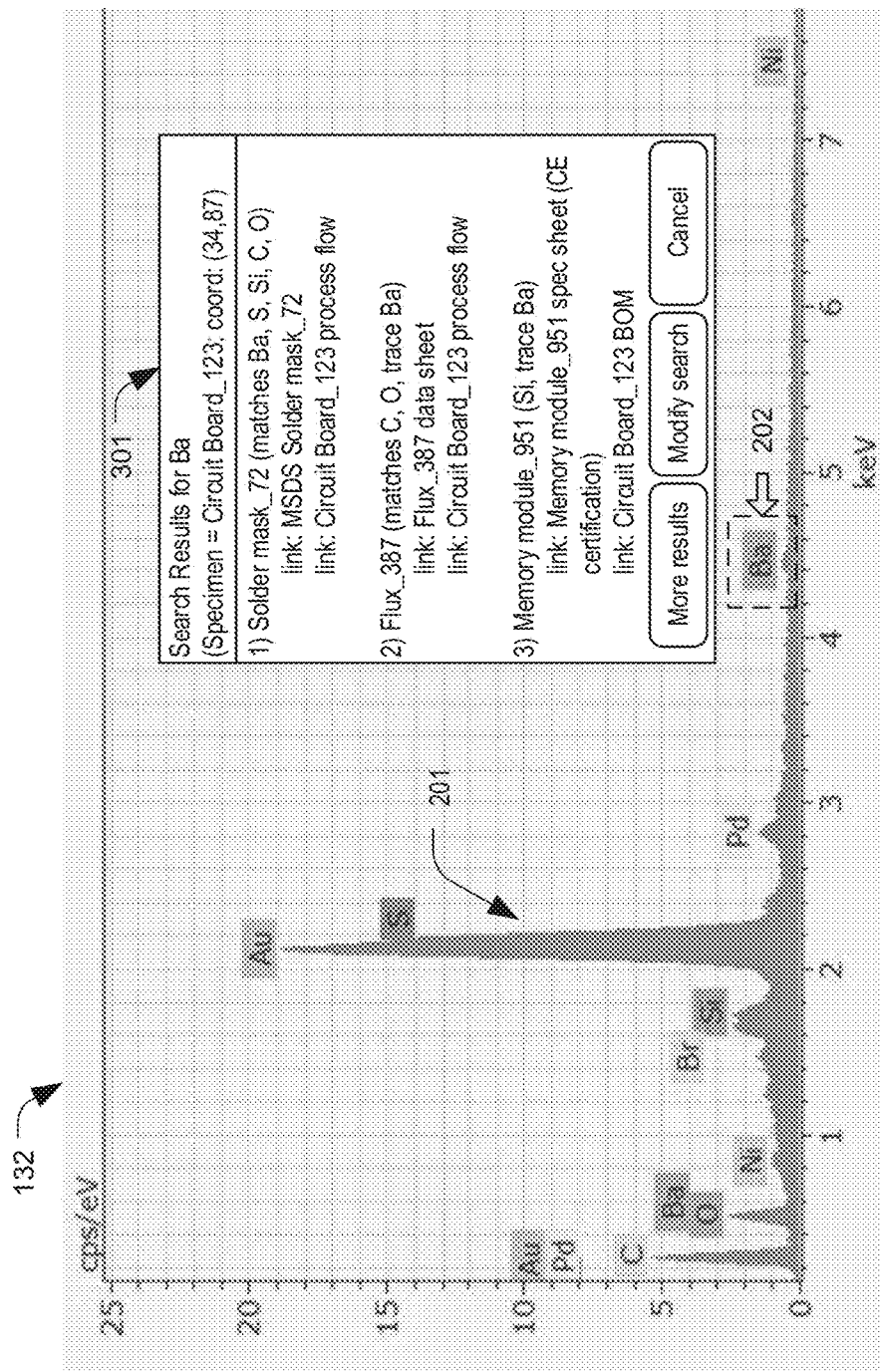
FIG. 3 is a graphical display of chemical analysis data and a search results generated by the system of FIG. 1, according to one embodiment.

FIG. 3 is a diagram depicting a graphical display 132 of the chemical analysis data 111, as generated by the system of FIG. 1. In FIG. 3, the graphical display 132 includes a search results display 301, according to a particular embodiment. The graphical display 132 may also display a set of spectral lines or peaks 201 that correspond to the chemical or elemental constituents of the specimen 120 and may display the targeted peak 202 as described with reference to FIG. 2.

The search results display 301 includes information generated in response to the search query 141. For example, the search results display 301 may include information retrieved from the proprietary databases 143, the public databases 144, or both. In the example illustrated in FIG. 3, the search results display 301 includes a list of search results (e.g., items 1-3 in the search results display), with each search result corresponding to a potential source of the chemical or elemental constituents corresponding to the target peak 202. For ease of reference, the chemical or elemental constituent corresponding to the target peak 202 is referred to herein as the target constituent. For example, in FIGS. 2 and 3, the target constituent is Barium. Thus, each search result in the search results display 301 includes Barium.

Each search result display 301 also includes information descriptive of each of the potential sources of the target constituent. For example, a first search result of the search result display 301 describes a solder mask ("solder mask_72") that includes Barium (Ba), Sulfur (S), Silicon (Si), Carbon (C), and Oxygen (O). The first search result also includes links to additional information about the solder mask, such as a link to a Material Safety Data Sheet (MSDS) associated with the solder mask and a link to a process flow that includes information descriptive of a process that uses the solder mask. As another example, a second search result of the search result display 301 describes a flux material ("flux_387") that includes Carbon (C), Oxygen (O) and traces of Barium (Ba). The second search result also includes links to additional information about the flux material, such as a link to a product datasheet associated with the flux material and a link to a process flow that includes information descriptive of a process that uses the flux material. As yet another example, a third search result of the search results display 301 describes a memory module ("memory module_951") that includes Silicon (Si) and traces of Barium (Ba). The third search result also includes links to additional information about the memory module, such as a link to a specification sheet that includes CE certification information and a link to a bill of materials (BOM) associated with the specimen analyzed to generate the chemical analysis data. Although three search results are illustrated in FIG. 3, in other embodiments, the search results display 301 may include more than three search results or fewer than three search results. Additionally, although each search result in FIG. 3 is shown as associated with two links to additional information, in other embodiments, one or more of the search results may be associated with more than two links to additional information or fewer than two links to additional information.

In a particular embodiment, search results may be sorted in the search results display 301 based on various criteria. For example, a sorting criterion may be specified by the user (e.g., as a user specified setting). As another example, a sorting criterion may be based on an indication of a likelihood that a potential source corresponding to a particular search result is the source of the target constituent in the chemical analysis data. The likelihood may be based, for example, on when or how the potential source is used during formation of the specimen.

As an example, the specimen may be analyzed to generate the chemical analysis data after a fifth process step. In this example, a first potential source (corresponding to a first search result) may be used during a fourth process step (immediately preceding the fifth process step), and a second potential source (corresponding to a second search result) may be used during a third process step (immediately preceding the fourth process step). In this example, the first potential source may be determined to be more likely to be the source of the target constituent since the fourth process step is closer in time to the chemical analysis than the third process step is.

As another example, the chemical analysis data may indicate the presence of the target constituent and at least one additional constituent. To illustrate, in FIG. 3, the chemical analysis data indicates the presence of the target constituent, Ba as well as additional constituents, including: Gold (Au), Palladium (Pd), Carbon (C), Oxygen (O), Nickel (Ni), Bromine (Br), and Silicon (Si), Sulfur (S). A search result that includes the target constituent and at least one of the additional constituents may be considered more likely to be the source of the target constituent than a search result that only includes the target constituent. Further, a search result that includes the target constituent and several of the additional constituents may be considered more likely to be the source of the target constituent than a search result that includes the target constituent and fewer of the additional constituents. To illustrate, in FIG. 3, the first search result includes Ba, S, Si, C, and O. Thus, the solder mask identified in the first search result matches the target constituent and four additional constituents present in the chemical analysis data. Thus, the first search result may be assigned a first likelihood value. In contrast, the second search result includes C, O, and trace Ba. Thus, the flux material identified in the second search result matches the target constituent and two additional constituents present in the chemical analysis data. Thus, the second search result may be assigned a second likelihood value that is lower than the first likelihood value. Accordingly, the second search result may be displayed in a less prominent position (e.g., lower in the list of search results) than the first search result.

As yet another example, the likelihood may be estimated based on a concentration of the target constituent in the potential source associated with each search result. To illustrate, in FIG. 3, the first search result indicates presence of Ba in the solder mask. In contrast, the second search result indicates that traces of Ba may be present in the flux material. Thus, the second search result may be assigned a lower likelihood value than the first search result based on an indication that the target constituent may have a lower concentration in the flux material than in the solder mask.

In some embodiments, more than one sorting criteria may be used at a time. For example, if two search results satisfy a first sorting criterion, a second sorting criterion may be used to assign relative priorities or likelihood values to the two search results. To illustrate, in FIG. 3, the second search result and the third search result both indicate that traces of the target constituent are present. Accordingly, different likelihood values may be assigned to the second search result and the third search result based on an order in which the second search result and the third search result are used during manufacturing of the specimen, based on presence or concentration of other constituents, etc.

Figure 4:
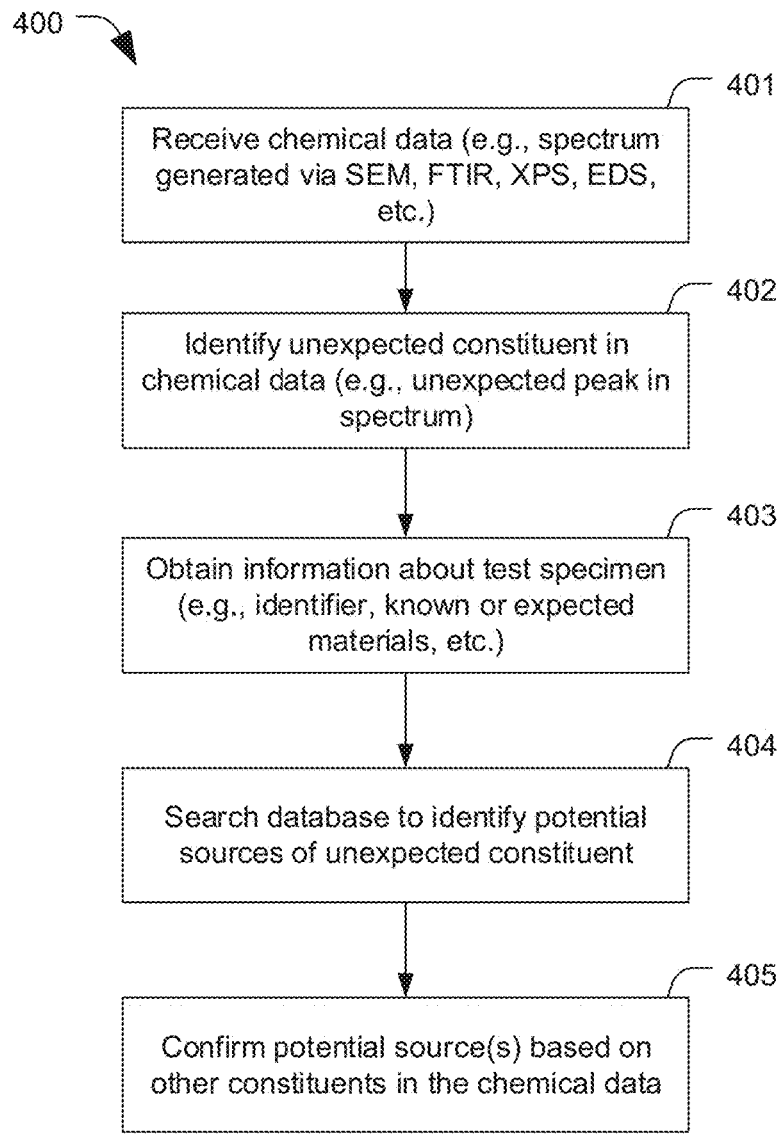
FIG. 4 is a flow diagram showing a particular embodiment of a method performed by the system of FIG. 1.

FIG. 4 is a flow diagram showing a particular embodiment of a method 400 that may be performed by the system of FIG. 1. The method 400 includes, at 401, receiving chemical data (e.g., a spectrum generated via SEM, FTIR, XPS, EDS, etc.). For example, the chemical data may include, be included within, or correspond to the chemical analysis data 111 of FIG. 1. To illustrate, the processor 102 of FIG. 1 may receive the chemical analysis data 111 from the sensors 110.

The method 400 also includes, at 402, identifying an unexpected constituent in chemical data (e.g., an unexpected peak in the spectrum). For example, the unexpected constituent may include a chemical or an element identified in the chemical data that is not identified in a set of expected constituents. The set of expected constituents may be identified based on information identifying a specimen analyzed to generate the chemical data. In another example, the unexpected constituent may be identified based on user input selecting the unexpected constituent via a graphical user interface, such as the graphical display 132 of FIGS. 1 and 2.

The method 400 also includes, at 403, obtaining information about a test specimen. The information about the test specimen may include the list of expected chemical or elemental constituents. As another example, the information about the test specimen may include the specimen identifier. The information about the test specimen may be obtained from a sensor (such as an optical or radiofrequency sensor). Alternatively, the information about the test specimen may be received via user input.

The method 400 includes, at 404, searching a database to identify potential sources of unexpected constituent. For example, a search request, such as the search query 141 of FIG. 1, may be generated based on the chemical data, information identifying the unexpected constituent, the information about the test specimen, or a combination thereof. The search request may be used to search one or more databases, such as one or more proprietary databases, one or more public databases, or a combination thereof.

The method 400 includes, at 405, confirming potential source(s) based on other constituents in the chemical data.

For example, search results may be generated based on the search request. For example, the search results may include, be included within, or correspond to the search results 145 of FIG. 1. The search results may be analyzed to facilitate identification of a source of the unexpected constituent. Thus, the method 400 facilitates determining potential sources of unexpected constituents in a specimen.

Figure 5:
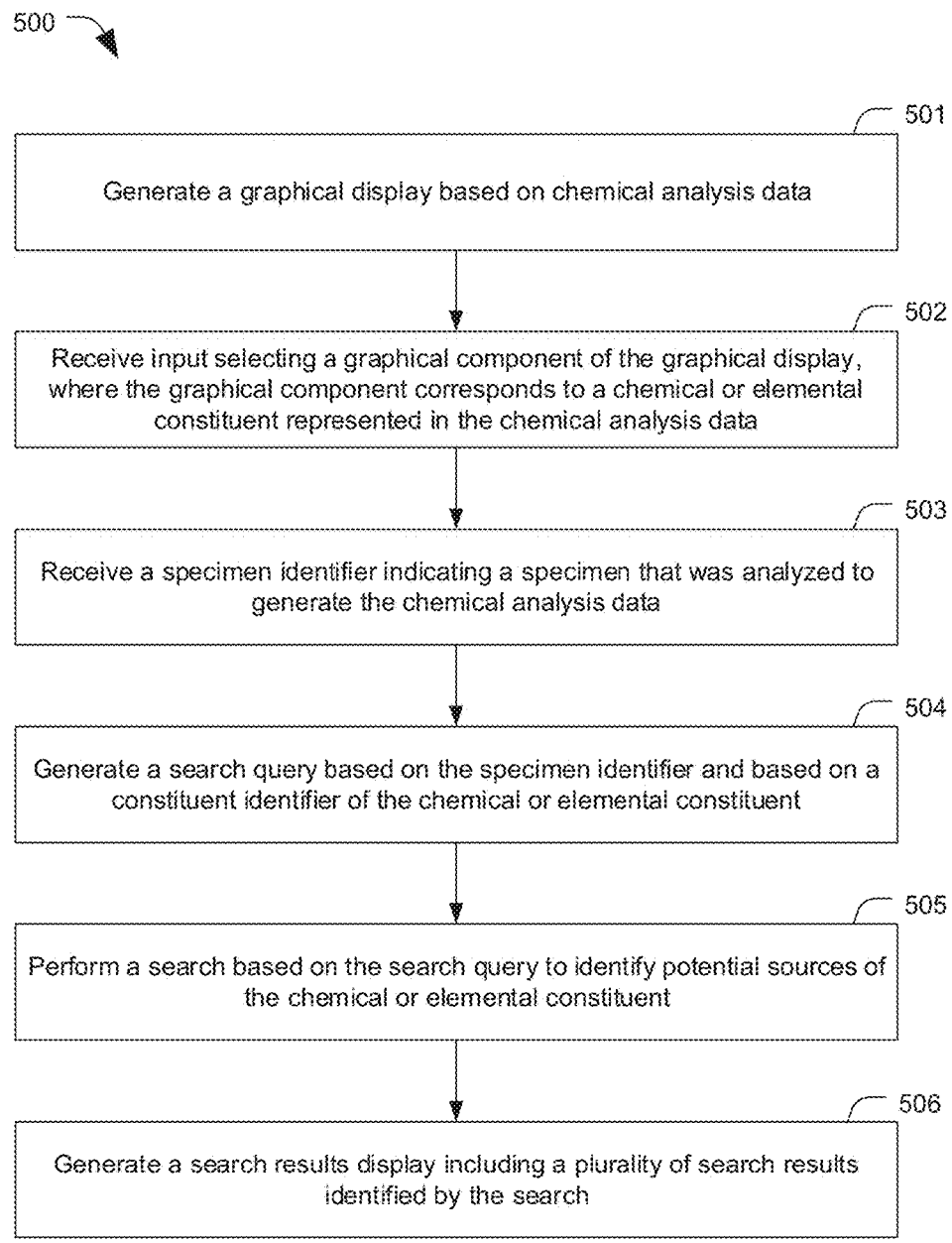
FIG. 5 is a flow diagram showing a particular embodiment of a method performed by the system of FIG. 1.

FIG. 5 is a flow diagram illustrating a particular embodiment of a method 500 that may be performed by the system of FIG. 1. The method 500 includes, at 501, generating a graphical display based on chemical analysis data. For example, the graphical display may include, be included within, or correspond to the graphical display 132 of FIGS. 1-3. The graphical display may include information descriptive of the chemical analysis data, such as spectral lines associated with chemical or elemental constituents of a specimen analyzed to generate the chemical analysis data.

The method 500 includes, at 502, receiving input selecting a graphical component of a graphical display, where the graphical component corresponds to a chemical or elemental constituent represented in chemical analysis data. For example, a user may select a peak or spectral line corresponding to the chemical or elemental constituent, as illustrated in FIG. 2. In another example, a computing device may automatically detect the chemical or element constituent by comparing the chemical analysis data to a list of expected chemical or elemental constituents associated with the specimen.

The method 500 includes, at 503, receiving a specimen identifier indicating a specimen that was analyzed to generate the chemical analysis data. For example, the specimen identifier may include a part number or part name associated with the specimen. In another example, the specimen identifier may identify a particular component or location on the specimen that was analyzed. The specimen identifier may be received via user input or may be generated automatically, e.g., by the one or more sensors 110 of FIG. 1.

The method 500 includes, at 504, generating a search query based on the specimen identifier and based on a constituent identifier of the chemical or elemental constituent. The search query may include, be included within, or correspond to the search query 141 of FIG. 1. The search query 141 may include a representation of the chemical analysis data 111, the representation including information descriptive of the chemical or elemental constituent and information descriptive of at least one second chemical or elemental constituent. For example, the constituent identifier, the specimen identifier, additional information, or a combination thereof, may be used to generate the search query.

The method 500 includes, at 505, performing a search based on the search query to identify potential sources of the chemical or elemental constituent. For example, the search query 141 may be used to search one or more databases, such as the proprietary databases 143 or the public databases 144 of FIG. 1. In an example, a database may include information descriptive of contaminant sources identified during analysis of similar specimens. In another example, a database include information descriptive of a bill of materials associated with the specimen 120. In this example, search results based on the search may identify components in the bill of materials that use the chemical or elemental constituent. As another example, a database may include information descriptive of one or more manufacturing processes used to form the specimen 120. In this example, search results based on the search may identify a manufacturing process that uses the chemical or elemental constituent.

The method 500 may also include, at 506, generating a search results display including a plurality of search results identified by the search. In a particular embodiment, the search results 145 may be sorted in the search results display 301 based, at least in part, on an order of manufacturing processes used to form the specimen 120. In another particular embodiment, the search results 145 may be sorted in the search results display 301 based, at least in part, on the presence of other constituents in the chemical data. For example, search results may include information identifying at least two potential sources of the chemical or elemental constituent (e.g., two chemicals used in forming the specimen). To illustrate, if the chemical or elemental constituent identified in the search query is Barium (as in the example of FIGS. 2-3), each source identified by a search result may include at least Barium. However, at least some of the search results may also include other chemical or elemental constituents (e.g., Carbon, Gold, Sulfur, etc.). The method 500 may include determining, for each potential source of the at least two potential sources, a corresponding additional constituents associated with the potential source. For example, a first potential source (corresponding to a first search result) may include Barium and a first additional constituent, such as Germanium, and a second potential source (corresponding to a second search result) may include Barium and a second additional constituent, such as Sulfur. The method 500 may also include generating a search results display in which the search results are sorted based, at least in part on, a presence of the corresponding additional constituents in chemical analysis data. To illustrate, continuing the example above, if the chemical data includes Germanium and does not include Sulfur, then the first search result may be displayed in a more prominent position than the second search result. Conversely, if the chemical data includes Sulfur and does not include Germanium, then the second search result may be displayed in a more prominent position than the first search result. If the chemical data includes both Sulfur and Germanium or includes neither Sulfur nor Germanium, then the display positions of the first and second search results may be determined based on other factors, such as a concentration of each of the additional constituents in the potential sources, a likelihood of each of the potential sources being a contaminant (e.g., based on how many manufacturing steps use each potential source, a relative order of manufacturing steps that use each potential source, results from prior analyses of similar specimens, user specified sorting preferences, etc.)

Figure 6:
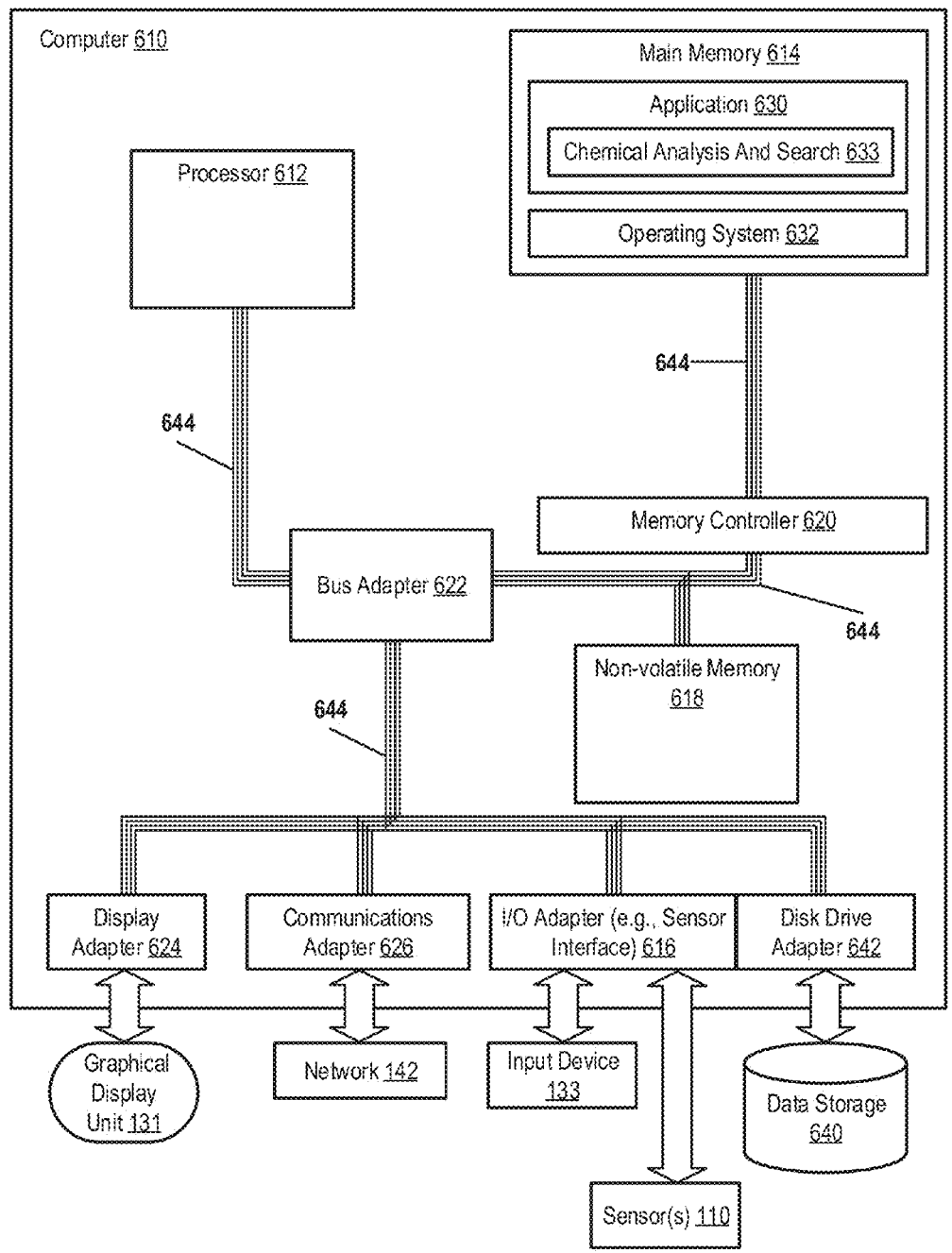
FIG. 6 is a diagram showing a particular embodiment of the elements of a computing device.

FIG. 6 depicts an illustrative, non-limiting example of a computer 610. The computer 610 may include, be included within, or correspond to the computing device 101 of FIG. 1. The computer 610 includes a processor 612, a main memory 614, an I/O adapter 616, a non-volatile memory 618, a memory controller 620, a bus adapter 622, a display adapter 624, a communications adapter 626, and a disk drive adapter 628. In a particular embodiment, the I/O adapter 616 may include a sensor interface to connect to one or more sensors 110.

The main memory 614 of the computer 610 includes software, such as an operating system 632 and software applications 630. For example, the software applications 630 may include a chemical analysis and search application 633. The chemical analysis and search application 633 may include, be included within, or correspond to one or more of the GUI engine 105, the search generator 106, or the search engine 107 of FIG. 1.

The display adapter 624 may be configured to interface with the graphical display unit 131. The communications adapter 626 may be configured to interface with the one or more networks 142. The disk drive adapter 628 may be configured to interface with a data storage device 640. One or more buses 644 or other communication circuitry may enable the various components of the computer 610 to communicate with one another.

The data storage device 640, the main memory 614, the non-volatile memory 618, or a combination thereof, may include computer-readable storage devices that store instructions executable by the processor 612 to cause the processor 612 to perform certain operations. For example, the operations may include generating a graphical display 132 on the graphical display unit 131 based on chemical analysis data 111. The chemical analysis data 111 may be obtained from the one or more sensors 110 coupled to the I/O adapter 616.

The operations may also include generating a search query 141 based on a specimen identifier and based on a constituent identifier. The specimen identifier may indicate a specimen 120 that was analyzed to generate the chemical analysis data 111, and the constituent identifier may correspond to a chemical or elemental constituent represented in the chemical analysis data 111. In some embodiments, the operations include receiving the user input 134 designating the specimen identifier and the constituent identifier. For example, the user input may be entered using the input device 133 coupled to the I/O adapter 616. The specimen identifier may designates a component of a circuit under test. In some embodiments, the chemical analysis data 111 includes an analysis spectrum and the constituent identifier is designated by selecting a peak of the analysis spectrum. In this example, the selected peak may correspond to a targeted peak 202 associated with a chemical or elemental constituent that would not typically be present in the specimen.

The operations may further include performing a search based on the search query 141 to identify potential sources of the chemical or elemental constituent, and generating a search results on the graphical display 132 including a plurality of search results 145 identified by the search. The search may be performed on proprietary databases 143 or public databases 144.

The previous description of the disclosed embodiments is provided to enable any person skilled in the art to make or use the disclosed embodiments. Various modifications to these embodiments will be readily apparent to those skilled in the art, and the generic principles defined herein may be applied to other embodiments without departing from the scope of the disclosure. Thus, the present disclosure is not intended to be limited to the embodiments shown herein but is to be accorded the widest scope possible consistent with the principles and features as defined by the following claims.

The invention claimed is:

1. A computing device to facilitate investigation of chemical or elemental constituents represented in chemical analysis data, the computing device comprising:
   a sensor interface to receive the chemical analysis data, which was generated by one or more sensors;
   one or more computer processors coupled to the sensor interface; and
   a memory storing instructions that are executable by the one or more computer processors to:

generate a graphical display based on the chemical analysis data;
receive input selecting a graphical component of the graphical display, wherein the graphical component corresponds to a chemical or elemental constituent represented in the chemical analysis data;
receive a specimen identifier indicating a specimen that was analyzed in order to generate the chemical analysis data;
generate a search query based on the specimen identifier and based further on a constituent identifier of the chemical or elemental constituent;
perform a search based on the search query in order to identify potential sources of the chemical or elemental constituent, wherein performing the search yields a set of search results identifying at least two potential sources of the chemical or elemental constituent;
determine, for each potential source of the at least two potential sources, a set of corresponding additional constituents associated with the respective, potential source; and
generate a search results display in which the set of search results is sorted based at least in part on a presence of the set of corresponding additional constituents in the chemical analysis data, wherein the search results display is output.

2. The computing device of claim 1, wherein the one or more sensors include an electron microscope.

3. The computing device of claim 1, wherein the one or more sensors include an energy dispersive spectroscopy sensor.

4. The computing device of claim 1, wherein the chemical analysis data includes an elemental analysis spectrum and wherein the graphical component corresponds to a peak of the elemental analysis spectrum.

5. The computing device of claim 1, wherein the specimen includes a component of a circuit.

6. The computing device of claim 5, wherein the specimen identifier includes an identifier of the circuit and an identifier of the component.

7. The computing device of claim 1, wherein the search query includes the specimen identifier, the constituent identifier, and an indication of a location on the specimen targeted to generate the chemical analysis data.

8. A computer-implemented method to facilitate investigation of chemical or elemental constituents represented in chemical analysis data, the computer-implemented method comprising:
generating a graphical display based on the chemical analysis data, wherein the chemical analysis data was generated by one or more sensors, wherein the graphical display is output;
receiving input selecting a graphical component of the graphical display, wherein the graphical component corresponds to a chemical or elemental constituent represented in the chemical analysis data;
receiving a specimen identifier indicating a specimen that was analyzed in order to generate the chemical analysis data;
generating a search query based on the specimen identifier and based further on a constituent identifier of the chemical or elemental constituent;
performing a search based on the search query in order to identify potential sources of the chemical or elemental constituent, wherein performing the search yields a set of search results identifying at least two potential sources of the chemical or elemental constituent;
determining, for each potential source of the at least two potential sources and by operation of one or more computer processors, a set of corresponding additional constituents associated with the respective, potential source; and
generating a search results display in which the set of search results is sorted based at least in part on a presence of the set of corresponding additional constituents in the chemical analysis data, wherein the search results display is output.

9. The computer-implemented method of claim 8, wherein performing the search includes using the search query to search a database that includes information descriptive of a bill of materials associated with the specimen and generating search results that identify components in the bill of materials that use the chemical or elemental constituent.

10. The computer-implemented method of claim 8, wherein performing the search includes using the search query to search a database that includes information descriptive of one or more manufacturing processes used to form the specimen and generating search results that identify a manufacturing process that uses the chemical or elemental constituent.

11. The computer-implemented method of claim 8, wherein performing the search includes using the search query to search a database that includes information descriptive of contaminant sources identified during analysis of similar specimens.

12. The computer-implemented method of claim 8, wherein the search query further includes a representation of the chemical analysis data, the representation including information descriptive of the chemical or elemental constituent and information descriptive of at least one second chemical or elemental constituent.

13. The computer-implemented method of claim 8, wherein the specimen identifier includes a part number or part name associated with the specimen.

14. The computer-implemented method of claim 8, the plurality of search results is further sorted in the search results display based, at least in part, on an order of manufacturing process steps used to form the specimen.

15. A non-transitory computer-readable medium storing instructions executable to perform operations to facilitate investigation of chemical or elemental constituents represented in chemical analysis data, the operations comprising:
generating a graphical display based on the chemical analysis data, wherein the chemical analysis data was generated by one or more sensors, wherein the graphical display is output;
receiving input selecting a graphical component of the graphical display, wherein the graphical component corresponds to a chemical or elemental constituent represented in the chemical analysis data;
receiving a specimen identifier indicating a specimen that was analyzed in order to generate the chemical analysis data;
generating a search query based on the specimen identifier and based further on a constituent identifier of the chemical or elemental constituent;
performing a search based on the search query in order to identify potential sources of the chemical or elemental constituent, wherein performing the search yields a set of search results identifying at least two potential sources of the chemical or elemental constituent;
determining, for each potential source of the at least two potential sources and by operation of one or more computer processors when executing the instructions, a set of corresponding additional constituents associated with the respective, potential source; and generating a search results display in which the set of search results is sorted based at least in part on a presence of the set of corresponding additional constituents in the chemical analysis data, wherein the search results display is output.

16. The non-transitory computer-readable medium of claim 15, wherein the operations further comprise receiving user input designating the specimen identifier and the constituent identifier.

17. The non-transitory computer-readable medium of claim 16, wherein the chemical analysis data includes an analysis spectrum, wherein the constituent identifier is designated by selecting a peak of the analysis spectrum.

18. The non-transitory computer-readable medium of claim 15, wherein the specimen identifier designates a component of a circuit under test.

19. The computer-implemented method of claim 8, wherein the one or more sensors include at least one of an electron microscope and an energy dispersive spectroscopy sensor.

20. The non-transitory computer-readable medium of claim 15, wherein the one or more sensors include at least one of an electron microscope and an energy dispersive spectroscopy sensor.

* * * * *